(12) United States Patent
Schiltges et al.

(10) Patent No.: US 7,419,484 B2
(45) Date of Patent: Sep. 2, 2008

(54) ADMINISTERING DEVICE WITH AN OSMOTIC DRIVE

(75) Inventors: Gilbert Schiltges, Kirchberg (CH); Axel Remde, Luetzelflueh (CH); Simone Geiser, Langenthal (CH); Catalin Cris, Ittigen (CH)

(73) Assignee: Disetronic Licensing AG, Burgdorf (CH)

( * ) Notice: Subject to any disclaimer, the term of this patent is extended or adjusted under 35 U.S.C. 154(b) by 401 days.

(21) Appl. No.: 11/041,913

(22) Filed: Jan. 24, 2005

(65) Prior Publication Data

US 2005/0182391 A1   Aug. 18, 2005

Related U.S. Application Data

(63) Continuation of application No. PCT/EP03/08174, filed on Jul. 24, 2003.

(51) Int. Cl.
*A61K 9/22* (2006.01)
(52) U.S. Cl. .................................. 604/892.1
(58) Field of Classification Search .......... 604/892.1, 604/65–67, 218, 143, 141, 151, 131
See application file for complete search history.

(56) References Cited

U.S. PATENT DOCUMENTS

| | | | |
|---|---|---|---|
| 2,655,919 A * | 10/1953 | Goodstein et al. ........... 604/148 |
| 3,527,216 A | 9/1970 | Snyder | |
| 3,760,804 A * | 9/1973 | Higuchi et al. ........... 604/892.1 |
| 4,351,335 A | 9/1982 | Whitney et al. | |
| 4,505,701 A | 3/1985 | Navato | |
| 4,513,034 A | 4/1985 | Sparer et al. | |
| 4,561,856 A | 12/1985 | Cochran | |
| 4,613,327 A | 9/1986 | Tegrarian et al. | |
| 4,773,900 A | 9/1988 | Cochran | |
| 4,838,862 A | 6/1989 | Baker et al. | |
| 5,169,390 A * | 12/1992 | Athayde et al. ............. 604/141 |
| 5,279,608 A * | 1/1994 | Cherif Cheikh .......... 604/892.1 |
| 5,722,399 A | 3/1998 | Chevallet et al. | |
| 5,769,824 A | 6/1998 | Hjertman et al. | |
| 5,869,078 A | 2/1999 | Baudino | |
| 6,287,295 B1 | 9/2001 | Chen et al. | |
| 6,348,043 B1 | 2/2002 | Hagen et al. | |
| 6,689,101 B2 | 2/2004 | Hjertman et al. | |
| 6,752,781 B2 | 6/2004 | Landau et al. | |
| 2002/0107477 A1 | 8/2002 | Kipfer | |
| 2002/0111589 A1 | 8/2002 | Michel | |

FOREIGN PATENT DOCUMENTS

| | | |
|---|---|---|
| DE | 196 47 701 A1 | 5/1998 |
| DE | 199 16 876 A1 | 11/2000 |
| DE | 199 55 368 A1 | 5/2001 |
| WO | WO 94/05354 | 3/1994 |
| WO | WO 2004/011062 A1 | 2/2004 |

* cited by examiner

*Primary Examiner*—Manuel A Mendez
(74) *Attorney, Agent, or Firm*—Dorsey & Whitney LLP

(57) ABSTRACT

An administering device with an osmotic drive for administering an injectable product includes a housing with a first chamber containing a solvent, a second chamber containing a solution and a product chamber for accommodating the product. A semi-permeable membrane is disposed between the first chamber and the second chamber. The second chamber is adjoined by a delivery means for delivering product out of the product chamber. A triggering device for triggering the osmotic drive includes an impermeable separating means between the first chamber and the second chamber. The delivery means is slidable relative to the housing along a longitudinal axis of the housing.

16 Claims, 4 Drawing Sheets

ADMINISTERING DEVICE WITH AN OSMOTIC DRIVE

CROSS-REFERENCE TO RELATED APPLICATION(S)

This application is a continuation of International Application No. PCT/EP2003/008174, filed on Jul. 24, 2003, which claims priority to German Application No. 102 33 622.9, filed on Jul. 24, 2002, the contents of which are incorporated herein by reference in their entirety.

BACKGROUND

The present invention relates to a device with an osmotic drive for administering an injectable product, in particular an infusion pump for administering insulin or the like over a long period of time.

In many medical or therapeutic applications, it is necessary or advantageous to administer a medicinal or therapeutic substance at a constant or variably adjustable continuous flow volume, rather than administering a large one-off dose of substance. For this purpose, it is common practice in in-patient treatment to mount infusion bottles containing a liquid substance above an injection point so that the liquid substance is delivered to the injection point via a hose connection by force of gravity. However, such infusion bottles are not suitable for use with an administering device in mobile applications or for administering relatively small doses over a long period.

Infusion pumps with a separate drive have therefore been developed, by means of which a product in a product container can be continuously delivered under pressure, enabling the product to be continuously dispensed from the container. U.S. Pat. No. 4,838,862, for example, discloses a portable infusion device with an osmotic drive, comprising a flat housing with several chambers lying one above the other and a laterally disposed outlet for the product. The uppermost chamber constitutes a solvent chamber, which is filled with water and is separated from a middle solution chamber filled with a salt solution by means of a fixed support plate, a porous layer disposed underneath and a semi-permeable membrane disposed under it. The fixed support plate has an orifice, which is sealed by means of a foil seal. A bottom product chamber is separated from the middle solution chamber by an elastic diaphragm. In the product chamber, the outlet for the product is provided in the form of a lateral orifice in the housing. The infusion device may be placed at a point on the body of a user by means of the base surface of the housing, for example, and carried in this manner. A push-button projects upwards out of the housing, disposed above the foil seal and has a needle pointing inwards into the water chamber in the direction of the foil seal. The infusion device is activated by pushing the push-button into the housing so that the needle pierces the foil seal and forces water out of the top water chamber through the orifice in the fixed support plate into the porous layer via the semi-permeable membrane. An osmotically induced pressure is generated in the middle solution chamber via the semi-permeable membrane by the water, which acts on the elastic diaphragm and hence on the product chamber. As a result of the pressure on the product chamber, the product is administered through the outlet at a continuous flow volume.

The elastic diaphragm of this known infusion device is disposed above the product chamber across a large surface area in order to create sufficient pressure in the chamber. Although the elastic diaphragm is able to camber inwards into the product chamber, this does not enable the product to be fully dispensed from the product chamber. Relative to the total surface area of the solvent chamber, the push-button overlaps with a small surface area. When the button is depressed, little pressure is generated in the solvent chamber, which mans that the solvent is distributed across the total surface of the semi-permeable membrane solely by the capillary action of the porous layer.

SUMMARY

An object of the present invention is to provide a device with an osmotic drive for administering an injectable infusion, and methods for its manufacture and use. Advantageously, the device can be stored for a longer period as a ready-to-use device, enables administration to be rapidly triggered, ensures a constant or variable flow volume, including also a small amount, continuously over a longer period, and provides for simple and reliable handling.

Accordingly, the device for administering an injectable product comprises a housing, in which an osmotic drive is accommodated. The housing is preferably of an elongate cylindrical shape, which advantageously enables a longitudinal axis to be defined, relative to which the individual components of the administering device are disposed. It would also be possible to choose a housing with any other shape, including one whereby the components are not disposed along an axis. For example, it would be possible to use a flat housing, in which case an administering device as proposed by the invention would be disposed along a longitudinal side. Other devices may be accommodated in the interior of the housing not occupied by the administering device, e.g., a display or control device for administering the injectable product.

For the osmotic drive, the housing accommodates a first chamber containing a solvent, a second chamber containing a solution and a product chamber for holding the product. The solvent might be water, for example, and the solution an over-saturated salt solution. It is advantageous to design the product chamber so that it is suitable for receiving a product container, such as a more or less conventional ampoule. This provides an easy means of enabling the administering device to be filled with product. Disposed between the first and the second chamber is a semi-permeable membrane, which is impermeable to the molecules of the solution and is osmotically active as soon as the solvent borders one side and the solution borders the other side. This creates the osmotic pressure needed to drive the administering device.

The administering device provided by the present invention also has a triggering device for triggering the osmotic drive. To this end, an impermeable separating means is provided between the first and the second chamber, which separates one of the liquids, the solvent or the solution, so that it does not come into contact with the semi-permeable membrane. The other respective liquid may already be in contact with the semi-permeable membrane. In order to trigger the osmotic drive, the impermeable separating means is pierced, so that the separated liquid is able to come into contact with the semi-permeable membrane. Another possible way of triggering the osmotic drive is to take out or pull out the impermeable separating means. This may be done via a slot, for example, provided with sealing elements which guarantee the seal when the impermeable separating means is in place as well as when it is removed. It is advantageous to provide the impermeable separating means at a point in the first or the second chamber from where it can be easily pierced by the triggering device or removed. A thin metal foil of aluminium or similar, for example, would constitute a suitable impermeable separating means. The triggering device incorporating the impermeable separating means prevents the drive from being set in motion whilst the administering device is being fitted. The device may therefore be prepared in a ready-to-use state. The osmotic drive merely has to be triggered in order to dispense a product.

For the purpose of the present invention, a delivery means is provided for delivering product out of the product chamber or out of the ampoule, which is slidable relative to the housing along a longitudinal axis of the housing. A suitable delivery means would be a plunger which acts on a stopper inside the ampoule, for example, or is directly the stopper in the ampoule. When the administering device is being operated, the delivery means directly adjoins the second chamber and can be pushed in the longitudinal direction of the housing inside the product chamber towards an outlet by means of the pressure prevailing in the chamber so that product is dispensed from the administering device. As a result of the osmotic drive, a continuous pressure is exerted on the delivery means so that a constant flow volume of the product can be produced.

The administering device provided by the present invention also enables the smallest volumes of product to be administered continuously over a longer period of time. There is no need to administer a one-off dose of highly concentrated or long-acting medicaments for example, such as would be used for an injection of long-acting insulin, the resorption of which depends on various parameters which can therefore fluctuate sharply as the action is released. Because dispensing takes place continuously over a longer time, fewer complications and fluctuations occur in the pharmacological kinetics and dynamics. Another advantage is the fact that the product flow volume can be interrupted at any time when administering a product using a device proposed by the invention. Complications incurred by administering too large product doses, which can lead to potentially dangerous states of health, e.g. hypoglycaemia if too large an amount of insulin is administered, can be avoided. Using an administering device of the type provided by the present invention, it is also possible to use ampoules that have already been pre-filled or have been filled by a user. This eliminates the inconvenience of having to fill the entire administration device. This being the case, it is advantageous that friction, which can occur between ampoule and stopper due to the high virtual osmotic pressure, for example, can be ignored. Furthermore, the product can be administered irrespective of the position of the administering device, which means that it can be easily carried on the body without having to use additional electrical power sources to drive a pump, for example.

In one embodiment of a device for administering an injectable product according to the present invention, the triggering device is the delivery means, in other words, in addition to delivering product, the delivery means is also used for triggering the osmotic drive. To this end, the delivery means is advantageously disposed so that it can be displaced relative to the housing opposite the direction in which the product is delivered. In other words, the delivery means is moved by the osmotic drive along the longitudinal axis of the administering device in the direction of delivery in order to deliver product from the product chamber, and the delivery means is moved exactly opposite the direction of delivery in order to trigger the osmotic drive. This being the case, the delivery means is disposed in such a way relative to the impermeable separating means that it is able to pierce the separating means due to the movement opposite the delivery direction, thereby triggering the osmotic drive. Accordingly, it is advantageous if the delivery means directly adjoins the second chamber containing the solution after having pierced the separating means so that the pressure in the chamber can be transmitted to the delivery means in order to deliver the product.

In this embodiment, the delivery means is provided in the form of a plunger, the longitudinal axis of which is disposed along the longitudinal direction of the housing, one end of which projects into the product chamber and one end face of which at the other end lies opposite the impermeable separating means, preferably face-on. The plunger is guided inside the housing so that it can be displaced towards the impermeable separating means. The plunger may be moved by inserting an ampoule in the product chamber, for example, which moves the plunger opposite the delivery direction towards the separating means. Accordingly, contact can advantageously be simultaneously made with a stopper inside the ampoule. The stopper is then pushed by the plunger inside the ampoule towards the outlet of the product chamber. At the same time as the ampoule is inserted and the osmotic drive is triggered, the administering device can be primed in order to bring the device into a starting position.

In one preferred embodiment, the first chamber is an annular chamber. The annular chamber is closed at one end and adjoins the second chamber at the other end. The cavity of the second chamber has a first region extending across the entire external diameter of the annular chamber and a second region with a smaller diameter extending centrally through the interior of the annular chamber as far as the product chamber. The impermeable separating means is therefore disposed where the region with the large diameter merges with the region having the small diameter, so that it separates the two regions of the second chamber as well as the second chamber from the first chamber. As long as the impermeable separating means is in place, the solution is disposed exclusively in the region of the second chamber which has the large diameter. The plunger may be disposed in the cylindrically shaped region with the small diameter, which means that, for the purpose of the invention, it can be moved both opposite the delivery direction towards the separating means in order to trigger the osmotic drive as well as in the delivery direction into the product chamber once the osmotic drive has been triggered.

In another embodiment of the device for administering an injectable product in accordance with the present invention, the triggering device is displaceable relative to the housing so that it is able to compress the interior of the first chamber containing the solvent. The triggering device used for this purpose is preferably a sleeve element which is slidable relative to the housing and separating means along the longitudinal axis. In one embodiment, it is more preferred if the sleeve element is provided in the form of a sleeve cap on an end of the housing lying opposite an end incorporating the product outlet. The sleeve element then forms the closure for one end face of the first chamber lying opposite the end at which an impermeable separating means is disposed. The separating means separates off a small region of the second chamber adjoined by the semi-permeable membrane which is not filled with solvent. The separating means and the semi-permeable membrane therefore lie opposite one another but have a clearance distance between them. The second chamber adjoins the semi-permeable membrane and is closed off by it. Adjoining the side of the second chamber lying opposite the membrane is a delivery means for delivering the product. The delivery means may be provided directly in the form of a stopper of an ampoule, which is slidable in the longitudinal direction of the ampoule towards the outlet.

In order to trigger the osmotic drive, the sleeve cap is pushed onto the housing of the administering device or is moved in translation in the delivery direction due to rotation by means of a thread. This motion compresses the first chamber, thereby building up a pressure in the chamber. The pressure acts on the impermeable separating means, which might be a thin foil, thereby destroying it, and the solvent from the first chamber moves into contact with the semi-permeable membrane. This triggers the osmotic drive, applies pressure to the second chamber and moves the stopper in the ampoule in the delivery direction. In order to prevent the triggering device from being undesirably triggered, a spacer may be provided between the sleeve cap and the housing, by means of which the translating motion of the sleeve cap along the longitudinal axis of the housing is blocked. This spacer is then removed for the triggering process. In this embodiment, the solvent rapidly comes directly into contact with a large surface area of the semi-permeable membrane and the osmotic pressure is rapidly applied.

In this embodiment, the administering device may already be pre-fitted with an ampoule and stopper and is filled with a desired product beforehand, ready for use. However, it would also be possible not to provide an ampoule in the administering device and the former may be used in the form of a finished component with a stopper which is inserted in the administering device as and when required. In this case, the second chamber containing the solution is closed off by a cover which has to be removed when inserting the ampoule to enable the stopper to come into contact with the second chamber.

Another advantage of an administering device in accordance with the present invention is that a pressure-reducing mechanism is provided as a means of reducing the pressure exerted on the delivery means by the osmotic drive. This enables the pressure exerted on the delivery means to be regulated, thereby controlling the volume of product flowing from the administering device. The pressure-reducing mechanism may be provided in the form of a third chamber, for example, disposed between the second chamber and the delivery means, which is connected to the second chamber via a pressure-reducing fluid connection. When the osmotic drive is triggered, the solution flows from the second chamber through the pressure-reducing fluid connection into the third chamber, where the prevailing pressure is then lower than in the second chamber. The delivery means directly adjoins the third chamber, so that it is driven in the delivery direction. The pressure-reducing fluid connection may be provided in the form of a capillary system or a spiral-shaped fluid passage, for example. A pressure-reducing mechanism of this type is known from patent application DE 199 39 023 A1 filed by this applicant, to which reference should be made.

The administering device provided by the present invention may also have a dispensing control device for controlling the product dispensed by the administering device. A simple valve may be used for this purpose, for example. However, it is more preferable to use a dispensing control device to which the product is dispensed from the product container, in which case the delivery means applies the product to an inlet of the dispensing control device so that the delivery means is uncoupled from the dispensing control device. A dispensing control device of this type is disclosed in applicant's German patent application DE 102 33 622, to which priority is claimed, and which is incorporated herein by reference.

For the purpose of the present invention, the dispensing control device may also incorporate a device for adjusting the permeability of the semi-permeable membrane. To this end, the materials used for the semi-permeable membrane are such that their permeability can be spacifically set on the basis of electromagnetic parameters, e.g., by electric voltage. An electronic system and a power source are provided in the dispensing control device in order to set the permeability. The dispensing control device is therefore able to control the osmotic pressure in such a way that a variable flow volume of the product is generated. Materials with an adjustable permeability are known from U.S. Pat. Nos. 4,513,034 and 5,869,078, for example.

With an administering device of the type provided by the present invention, it is possible to set up a continuous constant or alternatively variable flow volume, which can be adapted to a specific medicinal or therapeutic application. Since conventional ampoules are used, the administering device can easily be used for different substances and, because of the improved osmotic drive proposed by the invention, the substance is made available rapidly and easily.

DETAILED DESCRIPTION

Figure 1:
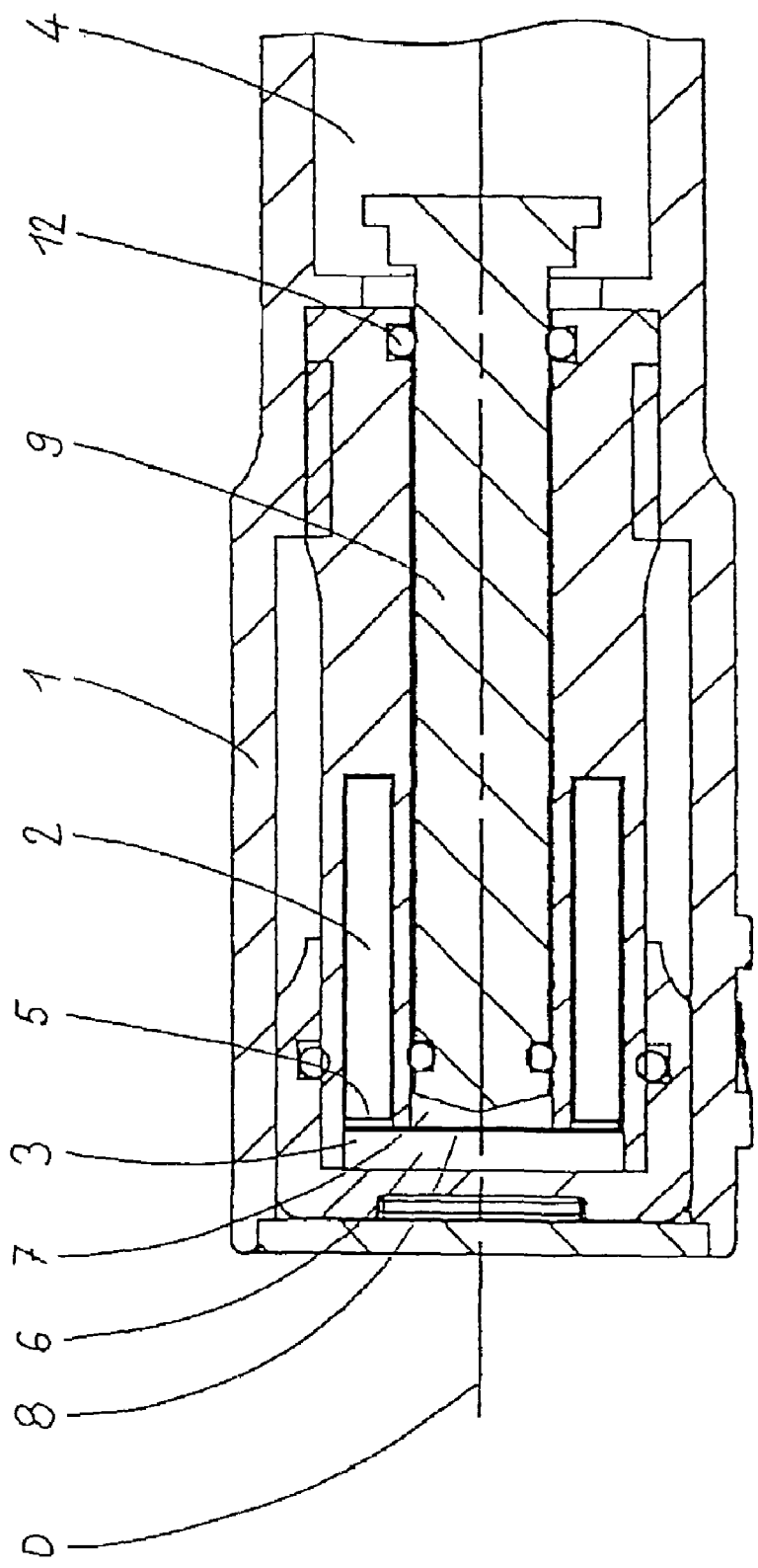
FIG. 1 shows a longitudinal section of a region of an administering device, in one embodiment, in the non-triggered state.

FIG. 1 shows the rear region of an embodiment of a device for administering an injectable product in accordance with the present invention. A housing 1 accommodates a first chamber 2 containing a solvent, a second chamber 3 containing an over-saturated salt solution and a product chamber 4, in which an ampoule containing the product, not illustrated in FIG. 1, can be inserted. The first chamber 2 is an annular chamber disposed concentrically about a longitudinal axis D of the housing 1. At one end, the first chamber 2 is closed off and at another end lying opposite the closed end, the first chamber 2 is closed off by a semi-permeable membrane 5. The cavity of the second chamber 3 extends in a first region 6 across the entire external diameter of the first chamber 2 and, in a second region 7 with a smaller diameter adjoining the first region 6, extends along the longitudinal axis D through the interior of the annular region of the first chamber 2 until it opens into the product chamber 4. The first region 6 and the second region 7 are separated from one another by an impermeable separating means in the form of a thin foil 8. The foil 8 extends across the entire, or substantially the entire, cross-sectional surface of the region 6 with the bigger diameter and lies with its outer region opposite and at a slight distance from the semi-permeable membrane mounted on the first chamber 2. When the administering device is in the non-triggered state, the salt solution is disposed exclusively in the first region 6 of the second chamber 3.

A plunger 9 is provided inside the second region 7 of the second chamber 3 as a delivery means for delivering product out of the product chamber 4, which extends almost across the entire length of the second region 7. At a first end, the plunger 9 lies with its end face opposite and at a slight distance from the foil 8. At the other end, the plunger 9 opens into the product chamber 4 and constitutes a drive surface 11 in conjunction with the end face at this end. The plunger 9 is disposed so that it can be displaced relative to the housing 1 inside the second chamber region 7 along the longitudinal axis D and is guided by the shape of the second region 7. Disposed between the plunger 9 and the wall of the second chamber region 7 are sealing means in the form of rubber rings 12, which seal the plunger off from the second region 7 and solvent as the administering device is being driven. The rubber rings 12 may also serve to stabilise the plunger 9 inside the second chamber region 7.

Figure 2:
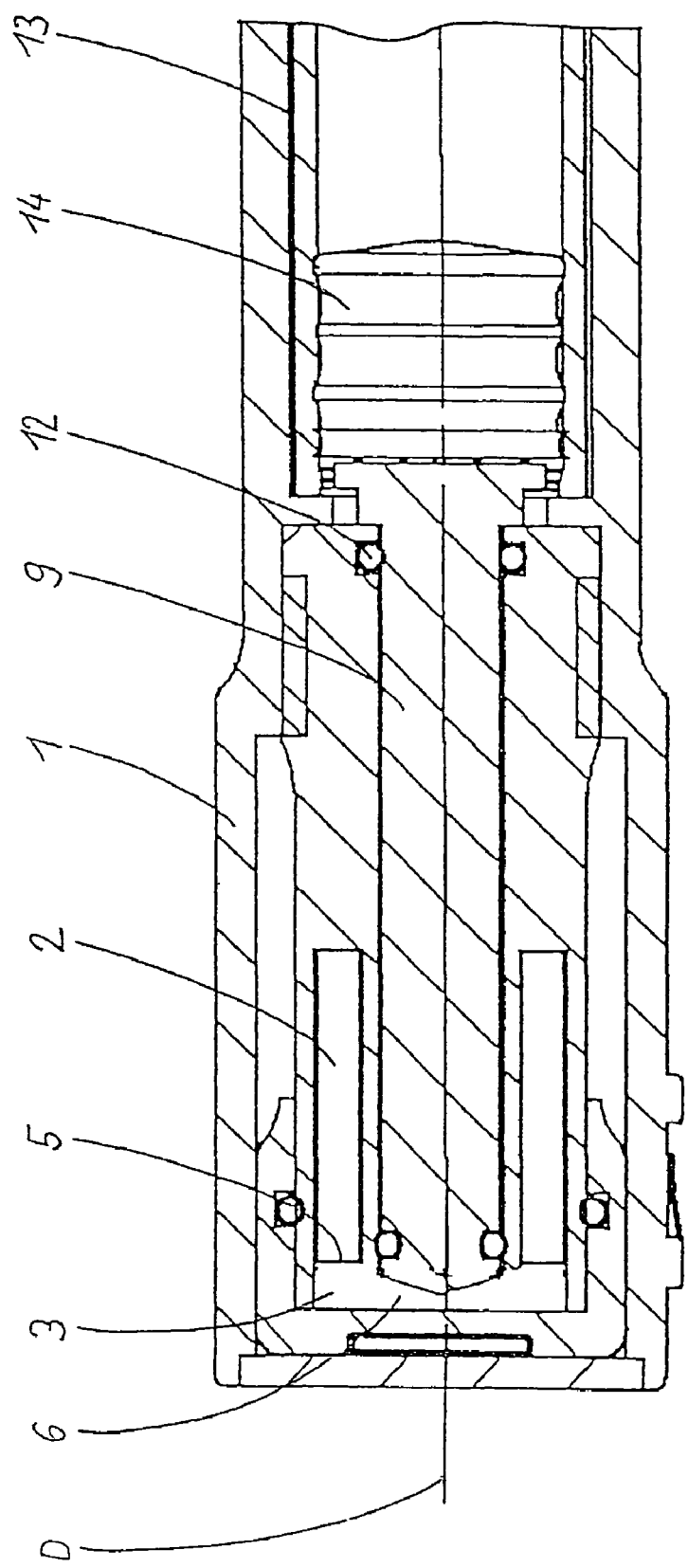
FIG. 2 shows a longitudinal section of the administering device illustrated in FIG. 1 in the triggered state.

FIG. 2 shows the embodiment of the administering device illustrated in FIG. 1, but in a triggered state. In this embodiment, the triggering device for triggering the osmotic drive comprises the impermeable foil 8 and the plunger 9 slidable along the longitudinal axis D of the housing 1. The administering device is triggered by moving the plunger 9 opposite the delivery direction of the product towards the foil 8 until it pierces the latter. The plunger 9 is moved in the direction towards the foil 8 by inserting an ampoule 13 in the product chamber 4. As the ampoule 13 is inserted, a stopper 14 hits the drive surface 11 of the plunger 9. An outlet of the ampoule lying opposite the stopper 14 (not illustrated) is initially closed so that the plunger 9 can be pushed due to contact with the stopper 14.

When the impermeable foil 8 is pierced, solvent reaches the semi-permeable membrane 5, thereby initiating the osmotic effect between the solution and the solvent. The osmotic pressure generated in the second chamber 3 as a result drives the plunger 9 along the longitudinal axis D in the delivery direction towards the stopper 14, as a result of which the solution penetrates the second region 7 of the second chamber 3. Once the outlet of the ampoule has been opened, the product can be dispensed from the ampoule 13 by means of the driven stopper 14. This being the case, the ampoule itself may be retained in the housing by means of an adapter. A connector or Luer fitted with a piercing needle may be provided on the adapter, for example, which is connected to the outlet and delivers the product to a desired point. The flow volume generated can be adapted to the specific requirements of a medicinal or therapeutic application by the choice of membrane material and the membrane geometry. The first chamber 2 containing the solvent is preferably filled with porous material, such as a non-woven material for example, which constantly conveys solvent to the semi-permeable membrane 5 by capillary forces. This ensures that the administering device will operate irrespective of its position.

Due to the principle of reverse osmosis, the osmotic procedure for generating pressure when driving the administering device can be reversed. The administering device can therefore be designed to be re-usable.

Figure 3:
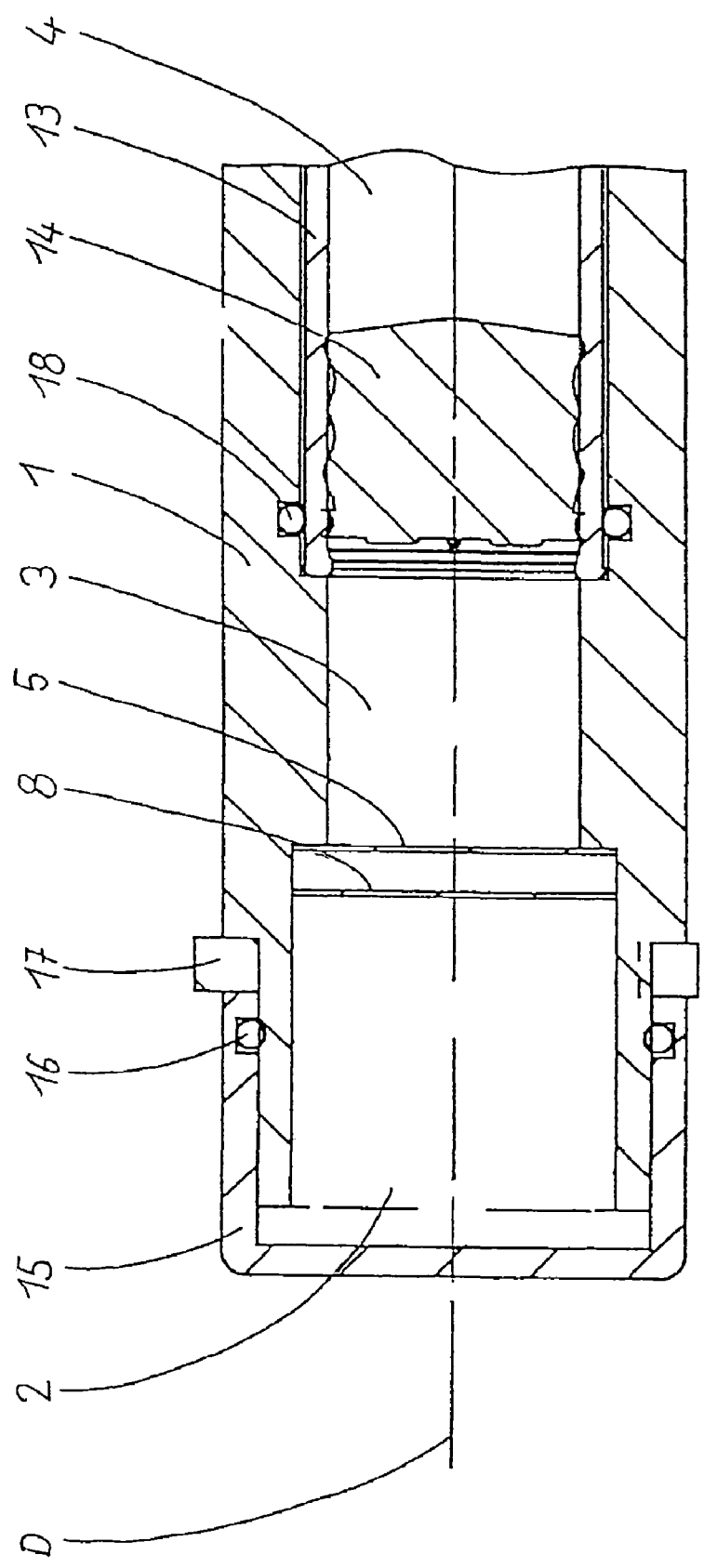
FIG. 3 shows a longitudinal section of a region of an administering device, in another embodiment, in the non-triggered state

FIG. 3 shows a partial view of another embodiment of the administering device in accord with the invention. The housing 1 accommodates a first chamber 2, a second chamber 3 and a product chamber 4. An ampoule 13 with a stopper 14 has already been inserted in the product chamber 4. The triggering device in this embodiment is a sleeve cap 15 which is slidable relative to the housing 1 along the longitudinal axis D of the housing 1. The sleeve cap 15 is sealed off from the housing and retained on it by rubber rings 16. The sleeve cap 15 is retained by a spacer 17 in a first position relative to the housing, in which the administering device is in a non-triggered state.

The sleeve cap 15 bounds one end of the first chamber 2 containing the solvent. At the oppositely lying end, the first chamber 2 is provided with an impermeable separating foil 8, which separates off a region of the chamber lying opposite the semi-permeable membrane 5. There is a clearance distance between the impermeable separating foil 8 and the semi-permeable membrane 5 so that the solvent in the first chamber 2 is not able to come into contact with the semi-permeable membrane 5. The semi-permeable membrane closes off the second chamber 3 at the end facing the first chamber 2.

At the end lying opposite the semi-permeable membrane 5, the second chamber 3 is closed off by the stopper 14. The stopper 14 is therefore in direct contact with the over-saturated salt solution in the second chamber 3. During operation of the administering device, the stopper 14 acts as a delivery means for delivering the product out of the ampoule 13. The seal between the ampoule 13 and the housing 1 is provided in the form of a rubber ring 18.

Figure 4:
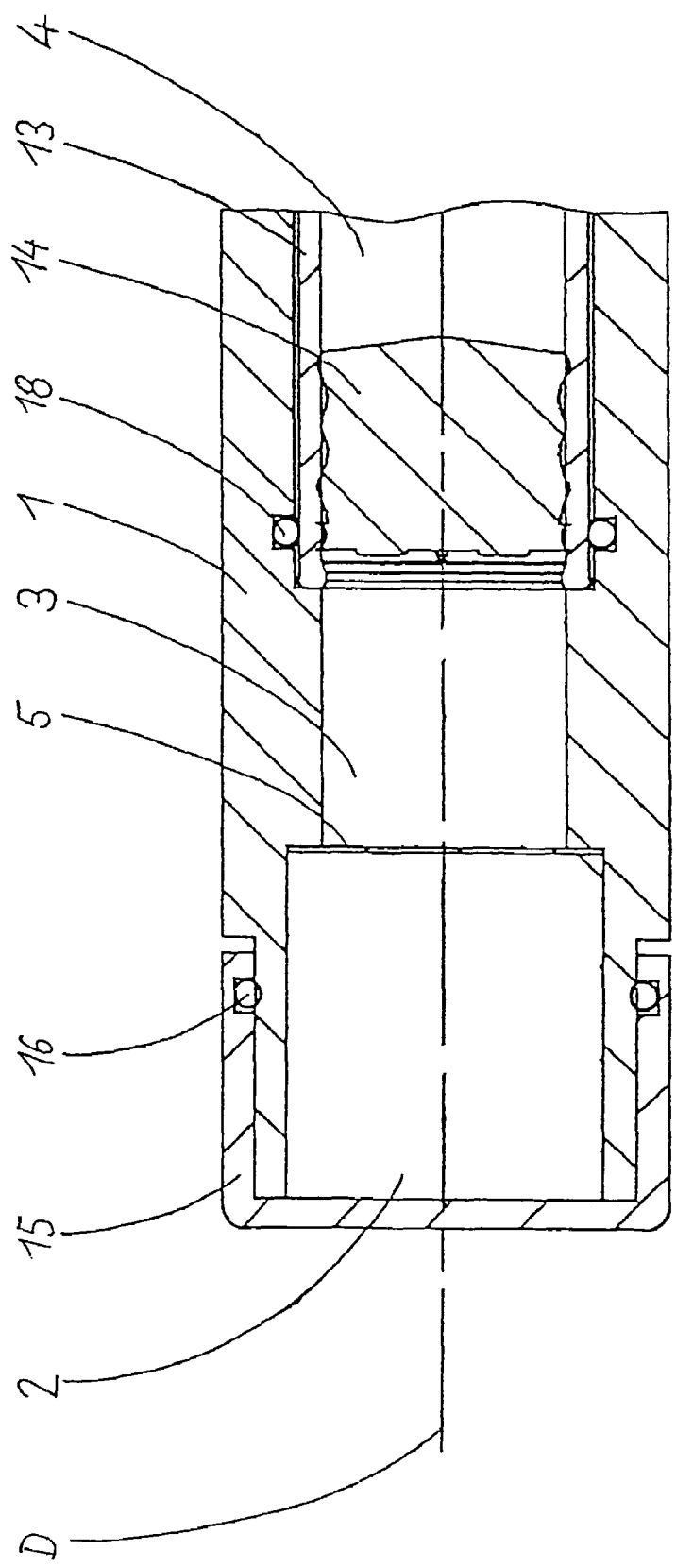
FIG. 4 shows a longitudinal section of an administering device illustrated in FIG. 3 in the triggered state.

FIG. 4 shows the administering device illustrated in FIG. 3 in a triggered state. The spacer 17 illustrated in FIG. 3 has been removed and the sleeve cap 15 pushed along the longitudinal axis D of the housing 1 in the direction towards the housing until it hits an edge of the housing. The sleeve cap 15 therefore applies a pressure to the impermeable foil 8, because it compresses the second chamber 3. As a result of the pressure applied, the impermeable foil 8 bursts and frees up access to the semi-permeable membrane 5 for the solvent. This activates the osmotic process and an osmotic pressure builds up in the second chamber 3, which acts directly on the stopper 14 in the ampoule 13. The stopper 14 is driven in the delivery direction and forces the product out of the ampoule 13 through an outlet (not illustrated) lying opposite the stopper 14.

In principle, it would also be possible to provide a pointed element on the internal face of the sleeve cap, lying opposite the impermeable foil 8, which projects out from the sleeve internal face in the direction of the foil 8 and terminates just short of it. As the sleeve cap 15 is pushed onto the housing, the pointed element pierces the foil 8 and assists the triggering process in order to trigger the osmotic drive.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device with an osmotic drive for administering an injectable product, comprising:
    a) a housing accommodating:
        a first chamber containing a solvent,
        a second chamber containing a solution, and
        a product chamber for holding the product;
    b) a semi-permeable membrane disposed between the first chamber and the second chamber;
    c) a delivery means for delivering product out of the product chamber; wherein
    d) a triggering device for triggering the osmotic drive incorporating an impermeable separating means is provided between the first chamber and the second chamber, and the delivery means is slidable relative to the housing along a longitudinal axis of the housing;
    wherein the triggering device is the delivery means.

2. An administering device as claimed in claim 1, wherein the triggering device is displaceable relative to the housing in a direction opposite that in which the product is delivered.

3. An administering device as claimed in claim 1, wherein the delivery means is provided as a means of piercing the impermeable separating means.

4. An administering device as claimed in claim 1, wherein the delivery means is a plunger guided inside the second chamber.

5. An administering device as claimed in claim 1, wherein the first chamber is an annular chamber disposed around the second chamber.

6. An administering device as claimed in claim 1, wherein the delivery means is displaced in the direction opposite the delivery direction by inserting a product container in the product chamber.

7. An administering device as claimed in claim 1, wherein the first chamber is filled with a porous material.

8. An administering device as claimed in claim 1, further comprising a device for adjusting permeability of the semi-permeable membrane.

9. A device with an osmotic drive for administering an injectable product, comprising:
   a) a housing accommodating:
      a first chamber containing a solvent,
      a second chamber containing a solution, and
      a product chamber for holding the product;
   b) a semi-permeable membrane disposed between the first chamber and the second chamber;
   c) a delivery means for delivering product out of the product chamber, the delivery means being slidable relative to the housing along a longitudinal axis of the housing; and
   d) a triggering device for triggering the osmotic drive, the triggering device incorporating an impermeable separating means and being provided between the first chamber and the second chamber;
   wherein the triggering device compresses the first chamber.

10. An administering device as claimed in claim 9, wherein the triggering device comprises a sleeve element slidable relative to the housing and separating means along the longitudinal axis.

11. A device with an osmotic drive for administering an injectable product, comprising:
   a) a housing accommodating:
      a first chamber containing a solvent,
      a second chamber containing a solution, and
      a product chamber for holding the product;
   b) a semi-permeable membrane disposed between the first chamber and the second chamber;
   c) a delivery means for delivering product out of the product chamber, the delivery means being slidable relative to the housing along a longitudinal axis of the housing;
   d) a triggering device for triggering the osmotic drive, the triggering device incorporating an impermeable separating means and being provided between the first chamber and the second chamber; and
   e) a pressure-reducing mechanism to reduce the pressure exerted on the delivery means due to pressure created in the second chamber.

12. An administering device as claimed in claim 11, further comprising a third chamber between the second chamber and the delivery means, said third chamber adjoined by the delivery means and connected to the second chamber via a pressure-reducing fluid connection.

13. An administering device as claimed in claim 12, wherein the pressure-reducing fluid connection is one of a capillary system or a spiral-shaped fluid passage.

14. An administering device as claimed in claim 11, further comprising a dispensing control device to control the product dispensed by the administering device.

15. An administering device as claimed in claim 14, wherein the delivery means applies the product to an outlet of the dispensing control device by pressure and the delivery means is uncoupled from the dispensing control device.

16. A device with an osmotic drive for administering an injectable product, comprising:
   a) a housing accommodating:
      a first chamber containing a solvent, the first chamber further being filled with a porous material,
      a second chamber containing a solution, and
      a product chamber for holding the product;
   b) a semi-permeable membrane disposed between the first chamber and the second chamber;
   c) a delivery means for delivering product out of the product chamber; wherein
   d) a triggering device for triggering the osmotic drive incorporating an impermeable separating means is provided between the first chamber and the second chamber, and the delivery means is slidable relative to the housing along a longitudinal axis of the housing.

\* \* \* \* \*